(12) United States Patent
Arfin et al.

(10) Patent No.: US 10,792,498 B2
(45) Date of Patent: Oct. 6, 2020

(54) EFFICIENT BACK TELEMETRY TRANSMISSION IN COCHLEAR IMPLANT SYSTEMS

(71) Applicants: ADVANCED BIONICS AG, Staefa (CH); Glen A. Griffith, Newbury Park, CA (US)

(72) Inventors: Scott Kenneth Arfin, Valencia, CA (US); Glen A. Griffith, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 280 days.

(21) Appl. No.: 16/067,493

(22) PCT Filed: Dec. 31, 2015

(86) PCT No.: PCT/US2015/068353
§ 371 (c)(1),
(2) Date: Jun. 29, 2018

(87) PCT Pub. No.: WO2017/116480
PCT Pub. Date: Jul. 6, 2017

(65) Prior Publication Data
US 2019/0022391 A1    Jan. 24, 2019

(51) Int. Cl.
*A61N 1/36*    (2006.01)
*A61N 1/372*    (2006.01)
(Continued)

(52) U.S. Cl.
CPC ......... *A61N 1/36039* (2017.08); *A61N 1/025* (2013.01); *A61N 1/36036* (2017.08);
(Continued)

(58) Field of Classification Search
None
See application file for complete search history.

(56) References Cited

U.S. PATENT DOCUMENTS

| 5,876,425 A | 3/1999 | Gord et al. |
| 6,073,050 A | 6/2000 | Griffith |

(Continued)

OTHER PUBLICATIONS

Bohorquez, et al., A 350 uW CMOS MSK Transmitter and 400 uW OOK Super-Regenerative Receiver for Medical Implant Communications, IEEE Journal of Solid-State Circuits, vol. 44, No. 4, Apr. 2009, pp. 1248-1259.

(Continued)

*Primary Examiner* — Ankit D Tejani
(74) *Attorney, Agent, or Firm* — ALG Intellectual Property, LLC

(57) ABSTRACT

A cochlear implant configured to be implanted within a patient may comprise an integrated circuit including a driver configured to generate a back telemetry signal encoded with information to be transmitted over a wireless communication link to a sound processor located external to the patient. The cochlear implant may also comprise a filter network that includes a first plurality of impedance components including a damping resistor, and a first and a second impedance component such as a capacitor or an inductor. The cochlear implant may also comprise an isolation network including a second plurality of impedance components configured to isolate, from the filter network and the driver, a forward telemetry signal received by the cochlear implant from the sound processor.

20 Claims, 9 Drawing Sheets

(51) Int. Cl.
*A61N 1/02* (2006.01)
*H04R 25/00* (2006.01)
*A61N 1/05* (2006.01)

(52) U.S. Cl.
CPC ....... *A61N 1/37223* (2013.01); *H04R 25/505* (2013.01); *H04R 25/554* (2013.01); *A61N 1/0541* (2013.01); *H04R 25/405* (2013.01); *H04R 2225/51* (2013.01); *H04R 2225/67* (2013.01); *H04R 2460/03* (2013.01)

(56) References Cited

U.S. PATENT DOCUMENTS

| | | | | |
|---|---|---|---|---|
| 6,415,186 B1* | 7/2002 | Chim | ................... | A61N 1/3787 607/57 |
| 7,092,763 B1* | 8/2006 | Griffith | ................ | H04R 25/558 607/57 |
| 8,275,462 B1* | 9/2012 | Griffith | ................ | A61N 1/3727 607/55 |
| 8,914,127 B1* | 12/2014 | Yan | ................... | A61N 1/36036 607/57 |
| 2006/0184213 A1 | 8/2006 | Griffith | | |

OTHER PUBLICATIONS

Harrison, et al., Wireless Neural/EMG Telemetry Systems for Small Freely Moving Animals, IEEE Transactions of Biomedical Circuits and Systems, vol. 5, No. 2, Apr. 2011, pp. 103-111.
International Search Report received in PCT Patent Application No. PCT/EP2015/068353, dated Mar. 29, 2016.

* cited by examiner

EFFICIENT BACK TELEMETRY TRANSMISSION IN COCHLEAR IMPLANT SYSTEMS

BACKGROUND INFORMATION

A cochlear implant system used to improve or enable hearing in a patient lacking full hearing capabilities may include components that are implanted within the patient, as well as components located external to the patient. The implanted components may be configured to communicate with the external components of the cochlear implant system by wireless telemetry over a wireless communication link. For example, external components may use forward telemetry to wirelessly transmit power and/or instructions to the components implanted within the patient. Likewise, the implanted components may use back telemetry to wirelessly transmit acknowledgement signals and/or diagnostic measurement data (e.g., signals representative of acquired neural response data measured within the patient by the implanted components in a clinical setting) back to the components external to the patient.

As cochlear implant systems evolve to offer improved functionality to patients, circuitry designed to generate and transmit back telemetry signals may be subject to aggressive operating specifications related to power supply voltages, power usage, space limitations, cost constraints, manufacturability, yield, etc. As a result, circuit designs that facilitate back telemetry operations within these aggressive operating specifications may provide significant advantages within modern cochlear implant systems.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
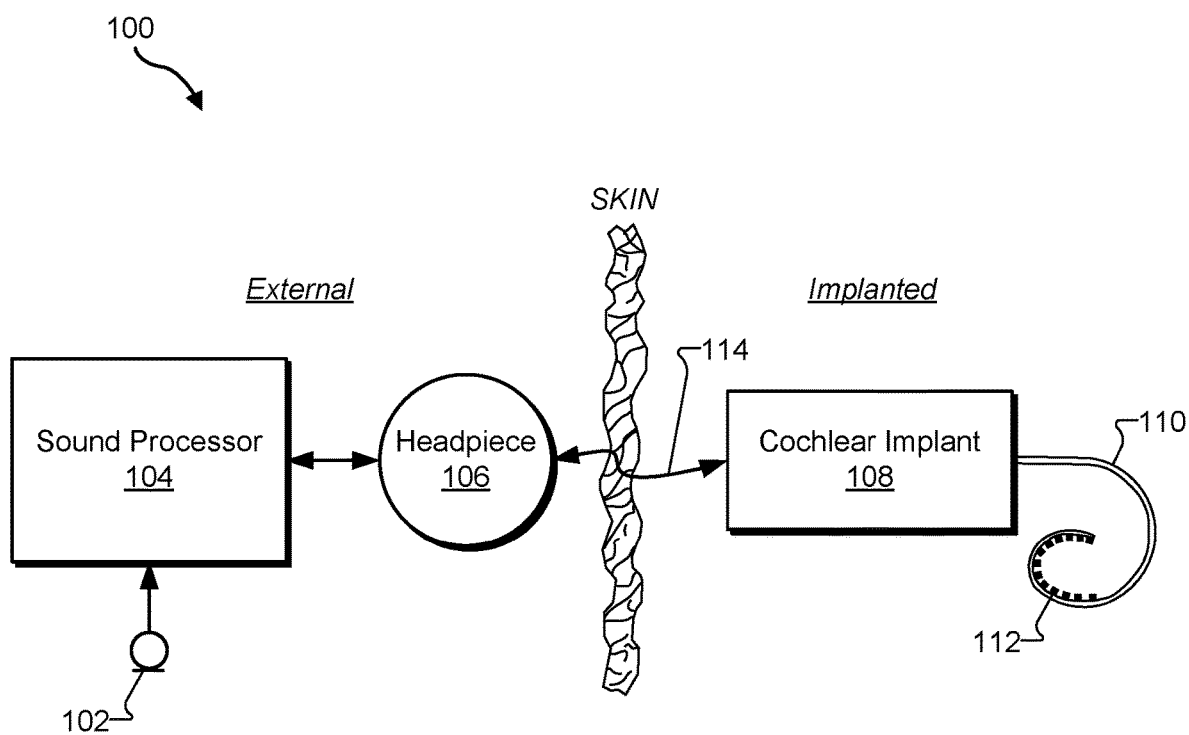
FIG. 1 illustrates an exemplary cochlear implant system according to principles described herein.

Cochlear implant systems with efficient back telemetry transmission are described herein. As will be described in more detail below, a cochlear implant configured to be implanted within a patient may include an integrated circuit configured to generate electrical stimulation for application to a cochlea of the patient. The integrated circuit may include a driver coupled to a power supply node and to a ground node and configured to generate a back telemetry signal at an output of the driver. The back telemetry signal may be encoded with information to be transmitted over a wireless communication link to a sound processor located external to the patient.

The cochlear implant may further include a filter network comprising an input node serially coupled to the output of the driver, an output node, and a first plurality of impedance components (e.g., capacitors, inductors, resistors, etc.). In certain embodiments, the impedance components of the filter network may include a damping resistor connected between the input node of the filter network and an internal node of the filter network, a first impedance component (e.g., a capacitor, an inductor, or a combination of thereof) connected between the internal node of the filter network and the output node of the filter network, and a second impedance component connected between the output node of the filter network and the ground node. In other embodiments, the impedance components of the filter network may include a first impedance component connected between the input node of the filter network and an internal node of the filter network, a second impedance component connected between the internal node of the filter network and the ground node, and a damping resistor connected between the internal node of the filter network and the output node of the filter network.

The cochlear implant may also include an isolation network serially coupled to the output node of the filter network. The isolation network may include a second plurality of impedance components configured to isolate a forward telemetry signal received by the cochlear implant from the sound processor from the filter network and the driver.

The systems described herein may allow a cochlear implant within a cochlear implant system to generate and transmit an efficient back telemetry signal. For example, the cochlear implant may generate a back telemetry signal at a particular power level, frequency, and bandwidth, and may transmit the back telemetry signal to a sound processor external to the patient within the cochlear implant system.

In some examples, one or more design goals for the back telemetry transmission may call for the back telemetry signal to be generated at particular power levels, frequencies, and/or bandwidths while subjecting the back telemetry circuitry to one or more design constraints. For example, a relatively low supply voltage (e.g., between approximately 1 and 3 Volts) may power the circuitry generating the back telemetry signal. Because the cochlear implant may operate using relatively little power, tight budgets may be imposed for how much of the total power of the cochlear implant may be used for back telemetry signaling rather than for other operations of the cochlear implant. Similarly, space constraints (i.e. constraints related to physical area used by components within an integrated circuit or on a circuit board) may be very restrictive on a cochlear implant since the cochlear implant will be implanted within a patient and, accordingly, it may be desirable for the cochlear implant to be as small and unobtrusive as possible. Moreover, budgets related to monetary costs of components included in the back telemetry circuitry may also be imposed to improve profits and/or control the cost to customers (e.g., patients) of the cochlear implant system. In certain examples, it may also be desirable to maintain backwards compatibility with legacy components and systems, even as the supply voltage, power budgets, space limitations, and/or cost constraints are tightened and/or otherwise modified. The systems described herein may provide flexibility and efficiency for back telemetry circuitry to facilitate meeting the design specifications and constraints described above. Specifically, as will be described in more detail below, the systems described herein may facilitate generating and transmitting back telemetry signals from low supply voltages using relatively low-cost components that use relatively little power and circuit board space.

Various embodiments of efficient back telemetry transmission in cochlear implant systems will now be described in reference to the figures.

FIG. 1 illustrates an exemplary cochlear implant system 100. As shown, cochlear implant system 100 may include various components configured to be located external to a user including, but not limited to, a microphone 102, a sound processor 104, and a headpiece 106. Cochlear implant system 100 may further include various components configured to be implanted within the user including, but not limited to, a cochlear implant 108 and a lead 110 (also referred to as an intracochlear electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the user. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a user.

In some examples, sound processor 104 may wirelessly transmit stimulation parameters (e.g., in the form of data words included in a forward telemetry signal) and/or power signals to cochlear implant 108 by way of a wireless communication link 114 between headpiece 106 and cochlear implant 108. Similarly, as will be described in more detail below, in the same or other examples, sound processor 104 may wirelessly receive acknowledgements and/or stimulation response data (e.g., included in a back telemetry signal) from cochlear implant 108 by way of wireless communication link 114. Accordingly, communication link 114 may include a bidirectional communication link and/or one or more dedicated unidirectional communication links. In some examples, sound processor 104 may execute and operate in accordance with a sound processing program that has been loaded into memory contained within sound processor 104.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the user's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bidirectional communication link and/or one or more dedicated unidirectional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a user and configured to apply stimulation to one or more stimulation sites located along an auditory pathway of a user.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the user via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Cochlear implant 108 may generate one or more back telemetry signals and transmit the signals over communication link 114 to headpiece 106 in order to communicate with sound processor 104. Specific examples of efficient back telemetry signals generated and transmitted by cochlear implant 108 will be described in more detail below.

Figure 2:
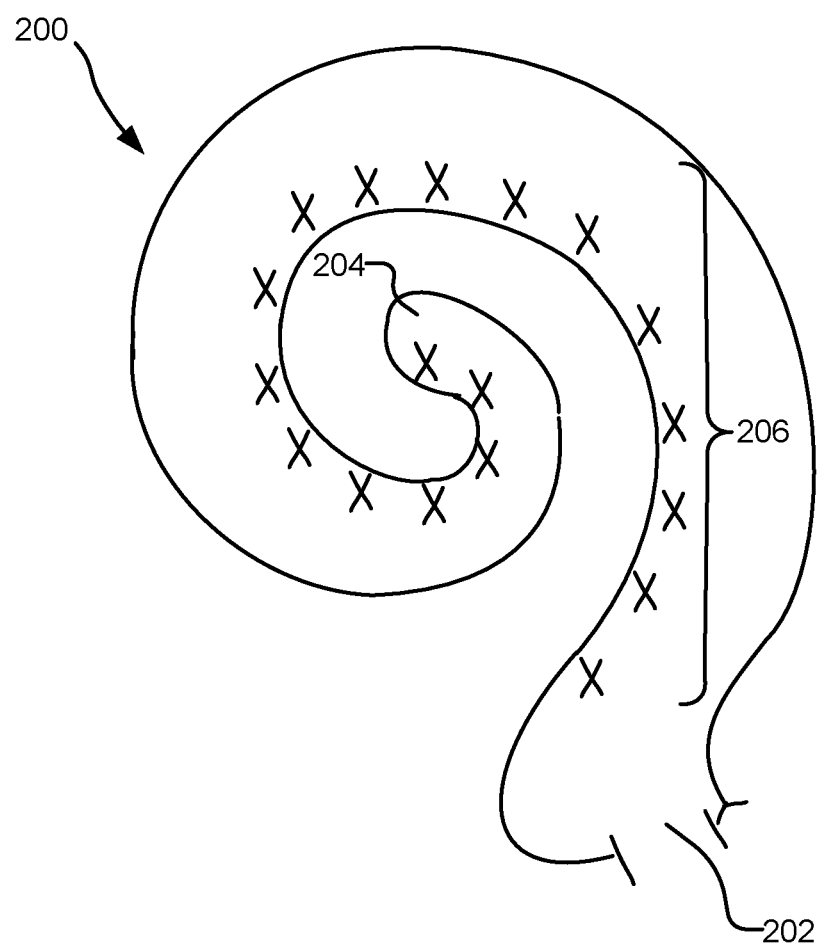
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

In some examples, a programming system separate from (i.e., not included within) cochlear implant system 100 may be selectively and communicatively coupled to sound processor 104 in order to perform one or more programming or fitting operations with respect to cochlear implant system 100. For example, the programming system may present audio clips to the patient by way of the cochlear implant system in order to facilitate evaluation of how well the cochlear implant system is performing for the patient. In response to instructions sent by sound processor 104, cochlear implant 108 may acknowledge the instructions and/or indicate that cochlear implant 108 is functioning properly. Additionally, cochlear implant 108 may measure or otherwise acquire data (e.g., neural response data) from within the patient and may communicate the data to sound processor 104. Communication from cochlear implant 108 to sound processor 104 may be performed wirelessly over communication link 114 using a back telemetry signal generated by cochlear implant 108.

Figure 3:
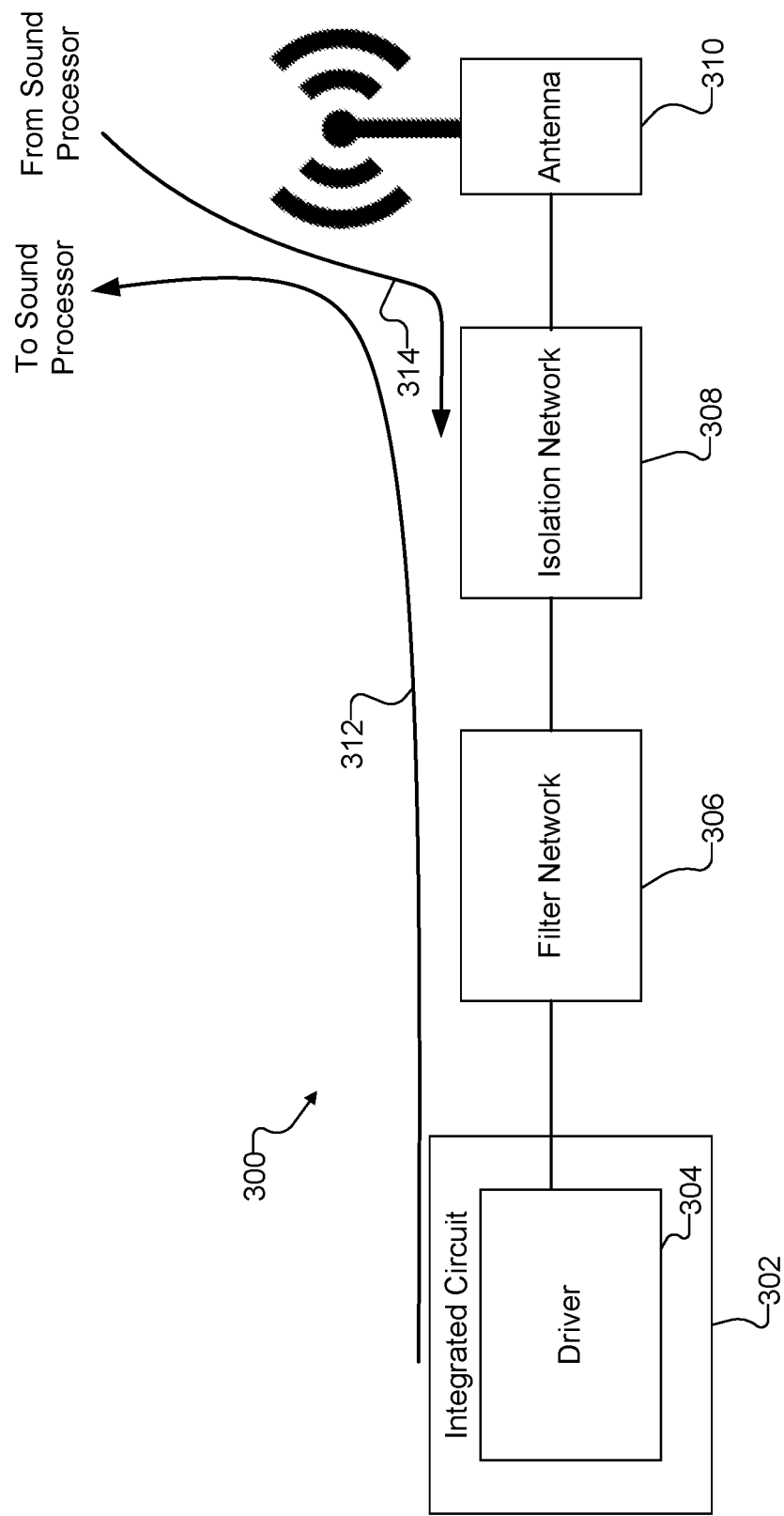
FIG. 3 illustrates an exemplary implementation of a cochlear implant according to principles described herein.

To this end, FIG. 3 illustrates exemplary components of an implementation of a cochlear implant 300 configured to generate and transmit an efficient back telemetry signal. Cochlear implant 300 may be an implementation of cochlear implant 108, described above in relation to FIG. 1. As shown in FIG. 3, cochlear implant 300 may include an integrated circuit 302 that includes a driver 304, a filter network 306 coupled to integrated circuit 302, an isolation network 308 coupled to filter network 306, and an antenna 310 coupled to isolation network 308. In certain embodiments, cochlear implant 300 may include more or fewer components than those shown in FIG. 3.

As used herein, a first component may be "coupled to" a second component when the first component is connected, directly or through one or more additional components, to the second component. The first component may be "directly coupled to" the second component when a connection between the first component and the second component does not include any additional components. Accordingly, for example, antenna 310 in FIG. 3 is shown as being coupled to integrated circuit 302 (i.e. through filter network 308 and isolation network 308), to filter network 306 (i.e. through isolation network 308), and to isolation network 308. However, antenna 310 is shown to be directly coupled only to isolation network 308.

As shown, cochlear implant 300 may generate and transmit a back telemetry signal 312 and receive a forward telemetry signal 314. For example, as indicated by the direction of back telemetry signal 312 in FIG. 3, back telemetry signal 312 may be generated by driver 304 within integrated circuit 302. Back telemetry signal 312 may then be processed by filter network 306 and/or by isolation network 308. Finally, back telemetry signal 312 may be transmitted by antenna 310. In certain examples, transmitting back telemetry signal 312 by antenna 310 may allow an external headpiece (e.g., headpiece 106 of FIG. 1) to receive back telemetry signal 312 and send it to an external sound processor (e.g., sound processor 104 of FIG. 1).

Similarly, forward telemetry signal 314 may be transmitted from a source external to cochlear implant 300, such as by the external headpiece as directed by the external sound processor. Forward telemetry signal 314 may be received by antenna 310 and may be processed by circuitry included in cochlear implant 300 (not explicitly shown). Forward telemetry signal 314 may then be delivered to integrated circuit 302 and/or to other components within cochlear implant 300 so that instructions included within forward telemetry signal 314 may be processed and executed and so that power included within forward telemetry signal 314 may be stored and/or otherwise processed and prepared for use by cochlear implant 300. As will be described below in more detail and as shown in FIG. 3, isolation network 308 may be configured to isolate forward telemetry signal 314 from circuits within cochlear implant 300 specifically configured for generating and processing back telemetry signal 312, which may be propagating in an opposite direction from forward telemetry signal 314. As such, forward telemetry signal 314 may be restricted from propagating past isolation network 308 and back telemetry signal 312 may be similarly restricted from propagating to circuitry configured specifically for processing forward telemetry signal 314 (e.g., circuitry not explicitly shown in FIG. 3). In certain examples, forward telemetry signal 314 may be received on a separate antenna (not shown) rather than on the same antenna 310 which transmits back telemetry signal 312. In these examples, isolation network 308 may be omitted from cochlear implant 300 and filter network 306 may be configured to interact directly with antenna 310.

Figure 4:
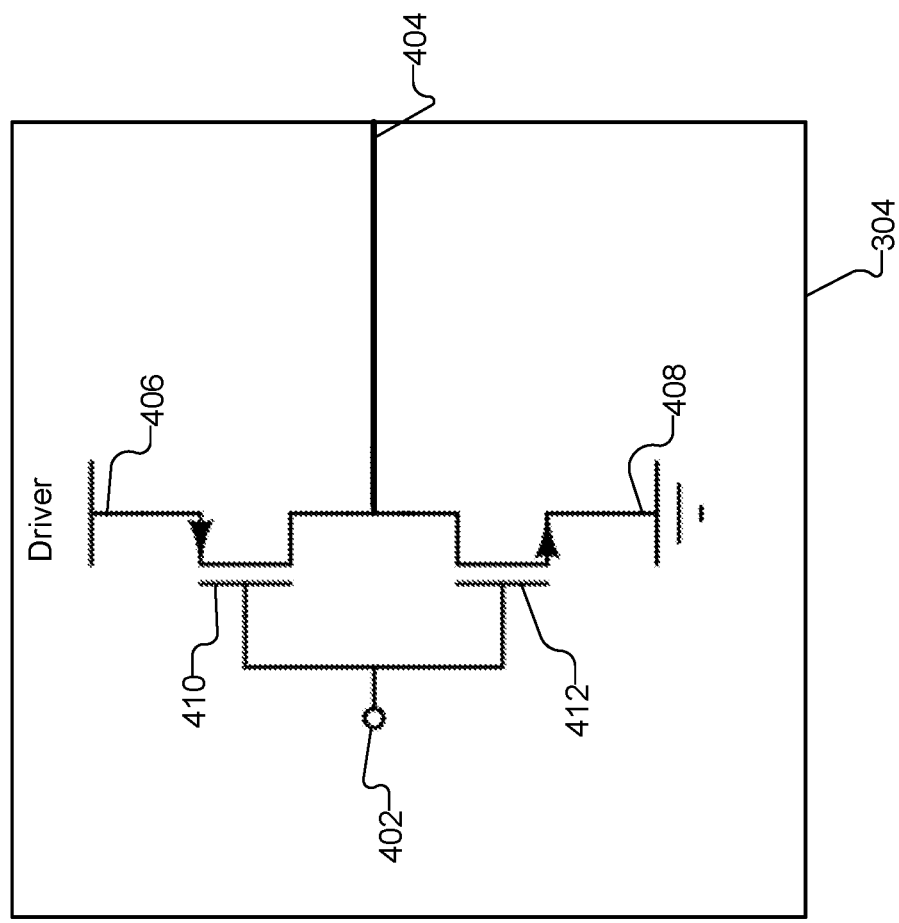
FIG. 4 illustrates an exemplary implementation of a driver used to generate a back telemetry signal within a cochlear implant according to principles described herein.

Each of the components illustrated within FIG. 3 will now be described in detail with reference to FIG. 3 and to detailed illustrations of each component in FIGS. 4 (driver 304), 5 (isolation network 308 and antenna 310), and 7-8 (filter network 306).

In FIG. 3, integrated circuit 302 may include a cochlear stimulation chip configured to facilitate some or all of the tasks performed by cochlear implant 300. For example, as described above in relation to cochlear implant 108 in FIG. 1, integrated circuit 302 may be coupled to a lead (e.g., similar or identical to lead 110 of FIG. 1, not explicitly shown in FIG. 3) having a plurality of electrodes disposed thereon (e.g., similar or identical to electrodes 112 of FIG. 1) and configured to be implanted within a cochlea of a patient associated with cochlear implant 300 to apply electrical stimulation to the cochlea. Integrated circuit 302 may receive, process, and/or execute instructions (e.g., instructions included with forward telemetry signal 314) sent by a sound processor (e.g., sound processor 104 of FIG. 1). For example, the instructions may cause integrated circuit 302 to apply electrical stimulation to the cochlea using the lead to stimulate hearing in the patient. In other examples, the instructions may cause integrated circuit 302 to perform one or more diagnostic tasks such as measuring a neural response to a particular stimulation to facilitate fitting and/or testing a cochlear implant system within a patient in a clinical setting. Additionally, integrated circuit 302 may process or facilitate processing of power received from an external source (e.g., headpiece 106 of FIG. 1) to provide power for cochlear implant 300.

As shown in FIG. 3, integrated circuit 302 may include driver 304 for generating back telemetry signals such as back telemetry signal 312. FIG. 4 illustrates an exemplary implementation of driver 304 used to generate back telemetry signal 312 within cochlear implant 300. As shown in FIG. 4, driver 304 may include an input node 402, an output node 404, a power supply node 406, a ground node 408, and one or more driver components 410 and 412.

Input node 402 may receive a signal encoded with information to be transmitted over a wireless communication link (e.g., wireless communication link 114 of FIG. 1). The signal coming into input node 402 may be amplified (e.g., by driver components 410 and/or 412) to become back telemetry signal 312, which, after being filtered and otherwise processed in back telemetry circuitry of cochlear implant 300 (e.g. filter network 306, isolation network 308, etc.), may be transmitted by antenna 310 to a sound processor. The signal coming into input node 402 may be generated by any suitable source. For example, the signal may be generated by other logic on integrated circuit 302 (not shown), by a lead coupled to integrated circuit 302 (e.g., lead 110 of FIG. 1), etc. The signal coming into input node 402 may be an analog signal or a digital signal.

Output node 404 may carry back telemetry signal 312 after it has been generated (e.g., after the signal at input 402 has been amplified by driver components 410 and/or 412). As such, output node 404 may be directly coupled with circuitry (e.g., within integrated circuit 302 or off-chip using discrete components) configured to process back telemetry signal 312. For example, as will be described in more detail below, components included in filter network 306 may be coupled (e.g., directly coupled) to output node 404 for resonating back telemetry signal 312 at a desired frequency, modifying (e.g., attenuating) a power level of back telemetry signal 312, or the like.

Power supply node 406 may be coupled to a power supply such as an off-chip power supply external to integrated circuit 302 or a power supply signal distributed to one or more components within integrated circuit 302 including driver 304. Power supply node 406 may provide power at any suitable voltage. For example, in certain implementations power supply node 406 may provide a relatively high voltage such as 3.0 V. In other implementations, power supply node 406 may provide a relatively low voltage less than approximately 1.5 V. For example, in certain cochlear implant systems (e.g., in relatively modern systems), power supply node 406 may provide power to driver at a voltage of approximately 1.1 V. The voltage at power supply node 406 may be defined in reference to ground node 408, which may provide a common return path for current throughout integrated circuit 302 and/or other components of cochlear implant 300. For example, ground node 408 may provide a return path for current flowing through driver components 410 and/or 412.

Driver components 410 and 412 may amplify the signal coming into input node 402 and output the amplified signal as back telemetry signal 312 at output node 404. Driver components 410 and 412 may be any components configured to suitably amplify the signal coming into input node 402. While two driver components are illustrated in FIG. 4, it will be understood that more or fewer components may be used in different implementations. As one example, the implementation illustrated in FIG. 4 shows complementary metal-oxide-semiconductor (CMOS) transistors used in an inverter configuration. In other examples, driver components 410 and 412 may include other types of transistors, one or more operational amplifiers, and/or other components suitable for amplifying the signal at input node 402 to generate back telemetry signal 312.

Referring back to FIG. 3, isolation network 308 is shown as being directly coupled to filter network 306, from which back telemetry signal 312 propagates, and to antenna 310, from which forward telemetry signal 314 propagates. As such, isolation network 308 may include one or more impedance components (e.g., resistors, capacitors, inductors, etc.) configured to pass back telemetry signal 312 to antenna 310, which may be configured to wirelessly transmit back telemetry signal 312. Antenna 310 may also be configured to receive forward telemetry signal 314, which isolation network 308 may be configured to block so that forward telemetry signal 314 does not propagate past isolation network 308 to filter network 306 and/or to driver 304. Impedance components within isolation network 308 and/or antenna 310 may be configured to operate in conjunction with one or more impedance components within filter network 306 to process back telemetry signal 312 as described below in reference to filter network 306.

To this end, isolation network 308 may be implemented as a band-pass filter that only allows signals at the frequency of back telemetry signal 312 to pass, or a band-stop filter that allows all frequencies to pass unaltered except for signals at the frequency of forward telemetry signal 314. For example, in an implementation where back telemetry signal 312 has a frequency of 10.7 MHz and forward telemetry signal 314 has a frequency of 49 MHz, isolation network 308 may include a band-pass filter configured to pass signals having a frequency of approximately 10.7 MHz, but to block all other frequencies. In other examples, isolation network 308 may include a band-stop filter configured to pass signals at all frequencies other than 49 MHz.

To implement the filtering and/or perform other operations described above, isolation network 108 may include any components that serve a particular implementation. For example, isolation network 108 may include a plurality of impedance components configured to isolate, from filter network 306 and/or driver 304, forward telemetry signal 314. More particularly, the plurality of impedance components may include a capacitor and an inductor connected in parallel between an output node of filter network 306 and an output node of isolation network 308.

Figure 5:
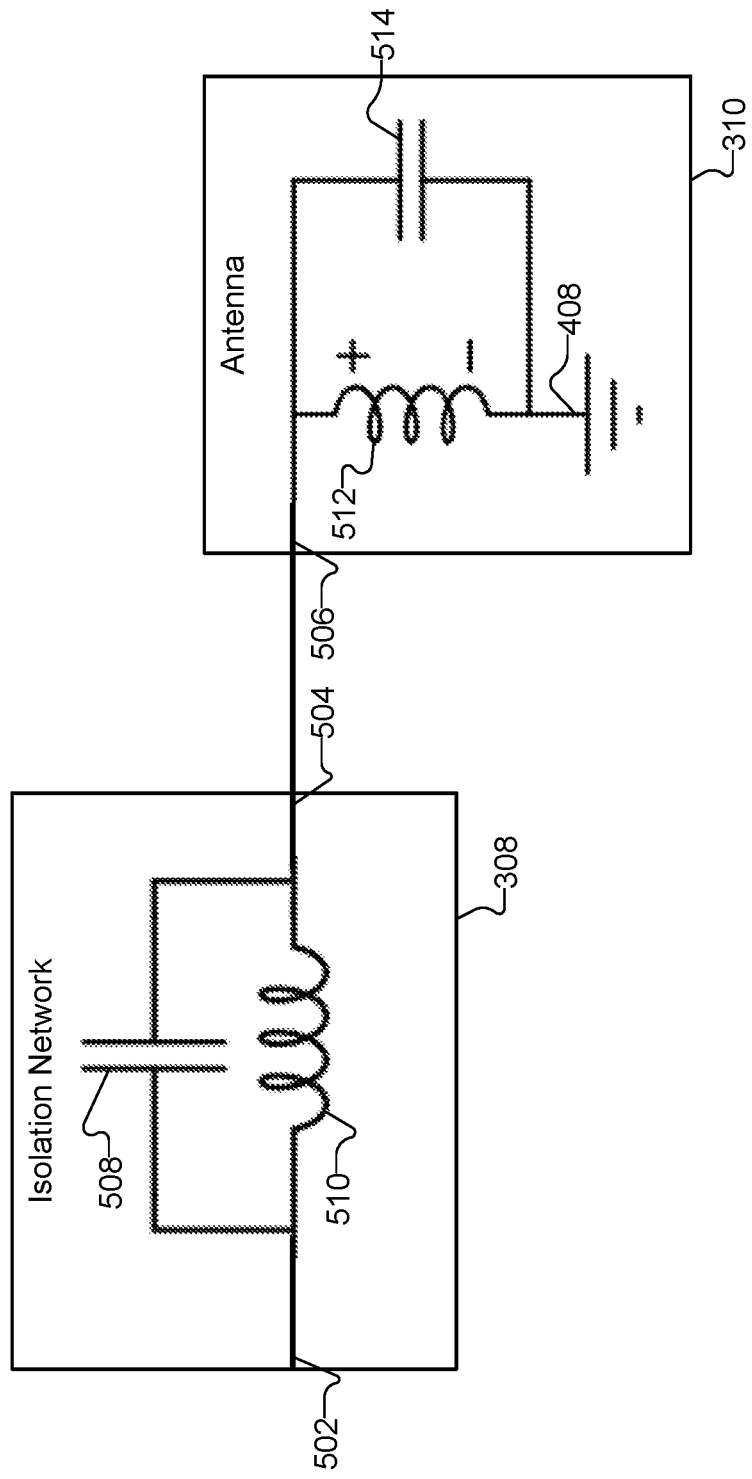
FIG. 5 illustrates an exemplary implementation of an isolation network and an exemplary antenna used to isolate and transmit a back telemetry signal within a cochlear implant according to principles described herein.

To illustrate, FIG. 5 shows an exemplary implementation of isolation network 308 and antenna 310 that may be used to isolate and transmit back telemetry signal 312 within cochlear implant 300. As shown in FIG. 5, isolation network 308 may include an input node 502 that may be directly coupled to an output node of filter network 306 (not shown in FIG. 5), and an output node 504 that may be directly coupled to an input node 506 of antenna 310. Isolation network 308 may include impedance components including a capacitor 508 and an inductor 510 which may be connected in parallel between input node 502 and output node 504. As described above, capacitor 508 and inductor 510 may be configured to separate back telemetry signal 312 from forward telemetry signal 314 by, for example, passing signals having a frequency within a range that includes a frequency of back telemetry signal 312 while blocking signals having a frequency within a range that includes a frequency of forward telemetry signal 314. In certain examples where antenna 310 is used to transmit back telemetry signal 312 but not to also receive forward telemetry signal 314, antenna 310 may be directly coupled to filter network 306 and isolation network 308 may be omitted.

As shown, antenna 310 may be coupled in series with isolation network 308 at output node 504 of isolation network 308 and input node 506 of antenna 310. Antenna 310 may facilitate telemetry over a wireless communication link (e.g., wireless communication link 114 of FIG. 1) between the cochlear implant and a sound processor (e.g., sound processor 104 of FIG. 1) by wirelessly transmitting back telemetry signal 312 to the sound processor and receiving forward telemetry signal 314 from the sound processor (e.g., by way of headpiece 106 of FIG. 1). As such, antenna 310 may be implemented by any suitable components to transmit signals (e.g., back telemetry signal 312) and receive signals (e.g., forward telemetry signal 314). For example, antenna 310 may include an implant coil corresponding to an external coil (e.g., located within headpiece 106) and configured to wirelessly (e.g., inductively) exchange telemetry signals such as back telemetry signal 312 and forward telemetry signal 314 through a skin flap of the patient. As shown in FIG. 5, antenna 310 may be represented within a circuit diagram by an implant coil comprising an inductor 512 and a capacitor 514 connected in parallel between input node 506 and ground node 408 (described above in relation to FIG. 4).

Returning to FIG. 3, filter network 306 may be coupled (e.g., directly coupled) to driver 304 within integrated circuit 302. As such, filter network 306 may receive back telemetry signal 312 from driver 304 as driver 304 generates back telemetry signal 312, and may process and/or pass back telemetry signal 312 through to isolation network 308.

Filter network 306 may process back telemetry signal 312 in any suitable way. For example, filter network 306 may include and/or be associated with a series resonator configured to resonate and/or perform filtering on back telemetry signal 312 (e.g., to convert back telemetry signal 312 from a square wave to a sinusoidal wave), and/or to set a bandwidth of back telemetry signal 312. Moreover, filter network 306 may be configured to modify (e.g., attenuate) a power level of back telemetry signal 312, and/or to process or perform other modifications to back telemetry signal 312 that may serve a particular implementation.

After processing back telemetry signal 312, filter network 306 may output the processed back telemetry signal 312 to isolation network 308. In certain examples, filter network 306 and isolation network 308 may operate in conjunction with one another to perform the tasks described herein for each of filter network 306 and isolation network 308. As such, filter network 306 and isolation network 308 may be combined or separated in any suitable way.

In certain examples, filter network 306 may be associated with (e.g., comprise or include one or more components for) a series resonator having a quality factor specifically set to a predetermined target value. A dimensionless quality factor (i.e. a "Q" or "Q factor") may be associated with a resonator and may be indicative of how under-damped the resonator is. For example, a resonator with a high quality factor may include very little damping, causing signals oscillating within the resonator to oscillate freely (i.e. losing very little energy during oscillation). Thus, in certain examples, a high quality factor may be desirable in a resonator to allow signals being processed by the resonator to oscillate efficiently. However, a resonator with a high quality factor may also have a very narrow bandwidth such that only signals that are precisely tuned to a particular frequency will resonate efficiently. Accordingly, in certain examples, it may also be desirable to limit the quality factor of a resonator to give the resonator a larger bandwidth, or, in other words, to ensure that signals having a frequency within a particular range will resonate efficiently within the resonator. For example, if a signal is oscillating at a frequency near the center frequency to which the resonator is tuned but not precisely at the center frequency, it may be desirable for the signal to still be resonated efficiently by the resonator.

Figure 6:
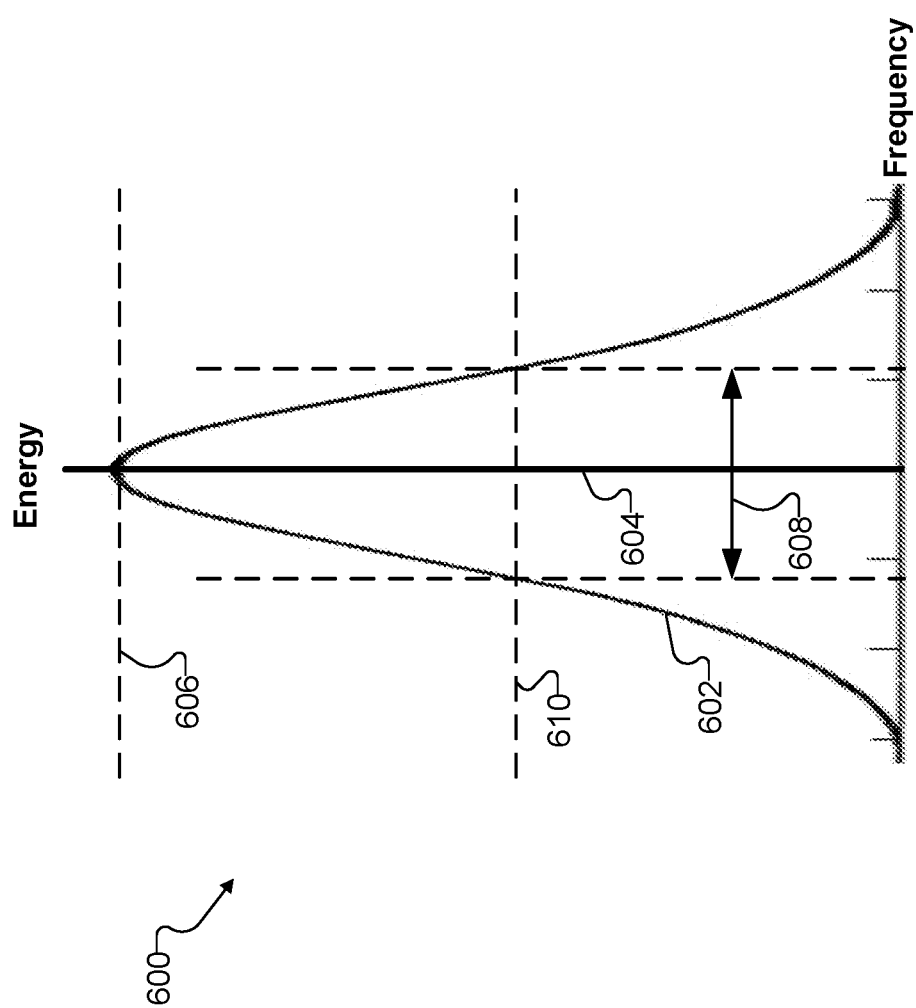
FIG. 6 illustrates a frequency response of a resonator associated with an exemplary filter network used to process a back telemetry signal within a cochlear implant according to principles described herein.

To illustrate, FIG. 6 shows a frequency response of an exemplary resonator associated with filter network 306 that may be used to process back telemetry signal 312 within cochlear implant 300. Specifically, FIG. 6 illustrates a graph 600 of an exemplary frequency response 602 of a resonator that may be associated with filter network 306. In FIG. 6, graph 600 illustrates frequency response 602 in the frequency domain, where frequency is represented along the horizontal axis and energy is represented along the vertical axis. As shown, frequency response 602 may be centered at a center frequency 604 and may have a peak energy level 606. A bandwidth 608 of the resonator may represent a range of frequencies at which the resonator stores energy within 3 dB of peak energy level 606 at center frequency 604. Accordingly, bandwidth 608 may correspond to a portion of frequency response 602 that is greater than a −3 dB energy level 610.

A quality factor of the resonator characterized by frequency response 602 may be determined by dividing center frequency 604 by bandwidth 608. Thus, for example, if bandwidth 608 is relatively narrow around center frequency 604, the resonator may have a relatively high quality factor. In other words, the resonator may be very efficient right at center frequency 604 (e.g., peak energy level 606 may be relatively high), but the resonator may be very inefficient at resonating signals with frequencies not precisely tuned to center frequency 604. Conversely, if bandwidth 608 is relatively wide around center frequency 604, the resonator may have a lower quality factor. In other words, in this case, the resonator may be less efficient right at center frequency 604 (e.g., peak energy level 606 may be lower), but the resonator may operate more efficiently for signals with frequencies that are near center frequency 604, even if the frequencies are not precisely tuned to center frequency 604.

A designer of a filter network such as filter network 306 may design a resonator associated with the filter network to have a particular frequency response. For example, the designer may select impedance components for use within the resonator to tune the resonator to efficiently resonate within a particular bandwidth 608 around a particular center frequency 604 matching a frequency of signals that the resonator is expected to process. In some implementations, it may be desirable for the designer to specifically configure the quality factor of the resonator to a value that is high enough to cause input signals to resonate efficiently but low enough to be compatible with input signals less precisely tuned to the center frequency. More specifically, the designer of filter network 306 may take into account various parameters associated with one or more upstream components being used to generate or perform upstream processing on back telemetry signal 312 (e.g., components within integrated circuit 302 and/or driver 304) such as accuracy, quality, and/or tolerances of the components to determine a frequency range around a center frequency at which the components will generate back telemetry signal 312. The designer may then design filter network 306 to have a particular quality factor that will process back telemetry signal 312 as efficiently as possible across the entire frequency range at which driver 304 is expected to generate back telemetry signal 312. For example, in certain embodiments, a quality factor associated with filter network 306 may be set within a range between approximately 5 and approximately 7.

Along with setting the quality factor (e.g., determined by center frequency 604 divided by bandwidth 608 within frequency response 602), filter network 306 may also be designed to set a power level at which back telemetry signal 312 resonates to a predetermined target value. For example, it may be desirable for back telemetry signal 312 to resonate at a power level great enough to be properly transmitted and received by external components (e.g., sound processor 104 and/or headpiece 106 of FIG. 1). At the same time, it may be desirable for back telemetry signal 312 to resonate at a power level small enough to remain within a planned power budget for generating back telemetry signal 312 to conserve overall power available to cochlear implant 300. Accordingly, in certain implementations, driver 304 may be configured to generate back telemetry signal 312 at a relatively high power level and filter network 306 may be configured to process back telemetry signal 312 to modify (e.g., attenuate) the power level to a desirable level that may be properly transmitted and received but that is within predetermined power budgets.

In some examples, filter network 306 may process back telemetry signal 312 to set the bandwidth of back telemetry signal 312 according to a predetermined quality factor, as well to set the power level transmitted through the resonance of back telemetry signal 312 to a predetermined power level. To this end, filter network 306 may perform the processing of back telemetry signal 312 in any suitable way. For example, filter network 306 may include one or more impedance components (e.g., resistors, capacitors, inductors, or any combination thereof) configured to perform the processing on back telemetry signal 312.

Figure 7:
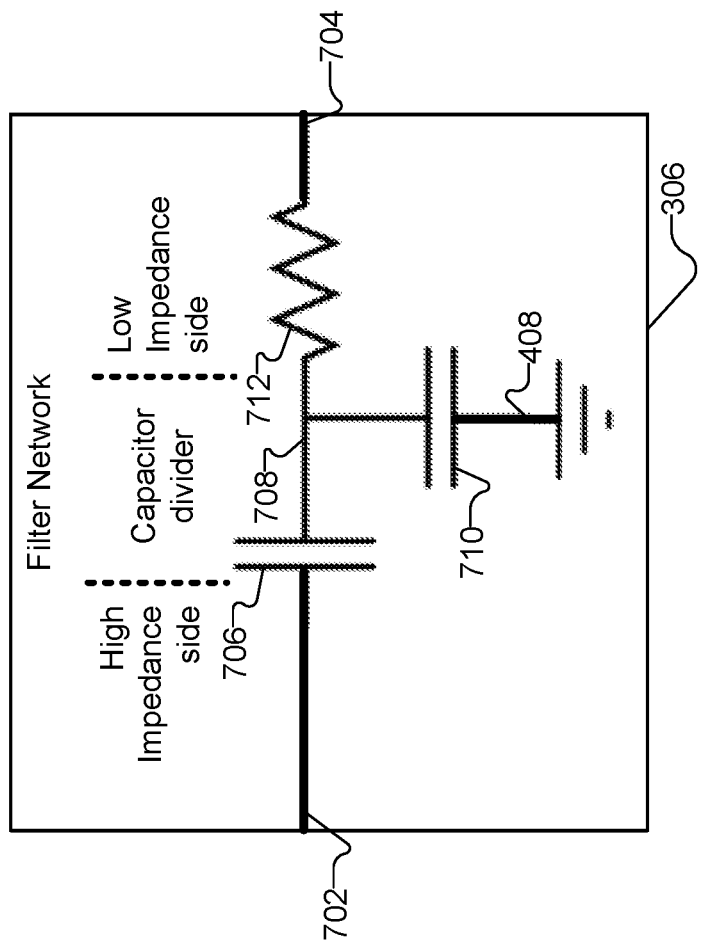
FIGS. 7-8 illustrate exemplary filter networks used to process back telemetry signals within a cochlear implant according to principles described herein.

To illustrate, FIG. 7 shows an exemplary embodiment of filter network 306 used to process back telemetry signal 312 within cochlear implant 300. As shown in FIG. 7, filter network 306 may comprise an input node 702, an output node 704, and a plurality of impedance components including a capacitor 706 connected between input node 702 and an internal node 708, a capacitor 710 connected between internal node 708 and ground node 408, and a damping resistor 712 connected between internal node 708 and output node 704. As illustrated above in relation to FIG. 3, input node 702 may be coupled (e.g., directly coupled) to an output node of driver 304 (e.g., output node 404 of FIG. 4), and output node 704 may be coupled (e.g., directly coupled) to an input node of isolation network 308 (e.g., input node 502 of FIG. 5). In other examples where isolation network 308 is omitted (not shown in FIG. 3), output node 704 may be coupled (e.g., directly coupled) to an input node of antenna 310 (e.g. input node 506 of FIG. 5).

In some examples, filter network 306 may be associated with an impedance divider circuit configured to set a power level at which back telemetry signal 312 resonates to a predetermined target value. An impedance divider circuit may include any suitable impedances to set (e.g., by attenuating and/or otherwise modifying) the power level to the predetermined target value. For example, the impedance divider circuit may use resistive impedances, capacitive impedances, and/or inductive impedances alone or in combination with one another. To illustrate one example, FIG. 7 shows a capacitive impedance divider circuit that includes capacitor 706 and capacitor 710. As shown, capacitor 706 and capacitor 710 may be configured as a capacitor divider to set a power level at which back telemetry signal 312 resonates to a predetermined target value that is lower than a natural power level that back telemetry signal 312 would have if filter network 306 included only capacitor 706 and not capacitor 710. In other examples, an inductive impedance divider circuit that includes inductors in place of capacitor 706 and capacitor 710 may be employed. For example, a capacitive impedance divider circuit (e.g., as shown in FIG. 7) may be used to set the power level to the predetermined target value in an embodiment where the back telemetry signal frequency is lesser than a forward telemetry signal frequency, while an inductive impedance divider circuit (not shown) may be used to set the power level to the predetermined target value in an embodiment where the forward telemetry signal frequency is lesser than the back telemetry signal frequency.

In the example shown in FIG. 7, a designer of filter network 306 may select impedance values of capacitors 706 and 710 such that the capacitor divider formed by capacitors 706 and 710 sets the power level of back telemetry signal 312 to the predetermined target value (e.g., a target value low enough to fit within a back telemetry power budget but high enough to be transmitted to and received by external components such as sound processor 104 and/or headpiece 106). As shown, the capacitor divider formed by capacitors 706 and 710 may have a high impedance side corresponding to where back telemetry signal 312 is input before being processed, and a low impedance side corresponding to where back telemetry signal 312 is output after being processed.

In certain examples, filter network 306 may be associated with a series resonator. For example, filter network 306 may be associated with an RLC resonator including a resistance component (e.g., damping resistor 712), a capacitive component (e.g., capacitor 706), and an inductive component (e.g., inductor 510 within isolation network 308 and/or inductor 512 within antenna 310 in FIG. 5). The resonator associated with filter network 306 may be characterized by a quality factor set by damping resistor 712 to a predetermined target value that is lower than a natural quality factor that the resonator would have if the resonator included only capacitor 706 and the inductive component (e.g., inductor 510 and/or inductor 512 of FIG. 5) and not damping resistor 712. As such, a designer of filter network 306 may select impedance values of damping resistor 712 to set the quality factor to the predetermined target value (e.g., a target value configured to resonate back telemetry signal 312 as efficiently as possible within a bandwidth that provides driver 304 with a suitable tolerance around the center frequency at which driver 304 generates back telemetry signal 312). As shown in FIG. 7, damping resistor 712 may be located on the low impedance side of the capacitor divider formed by capacitor 706 and capacitor 710.

Figure 8:
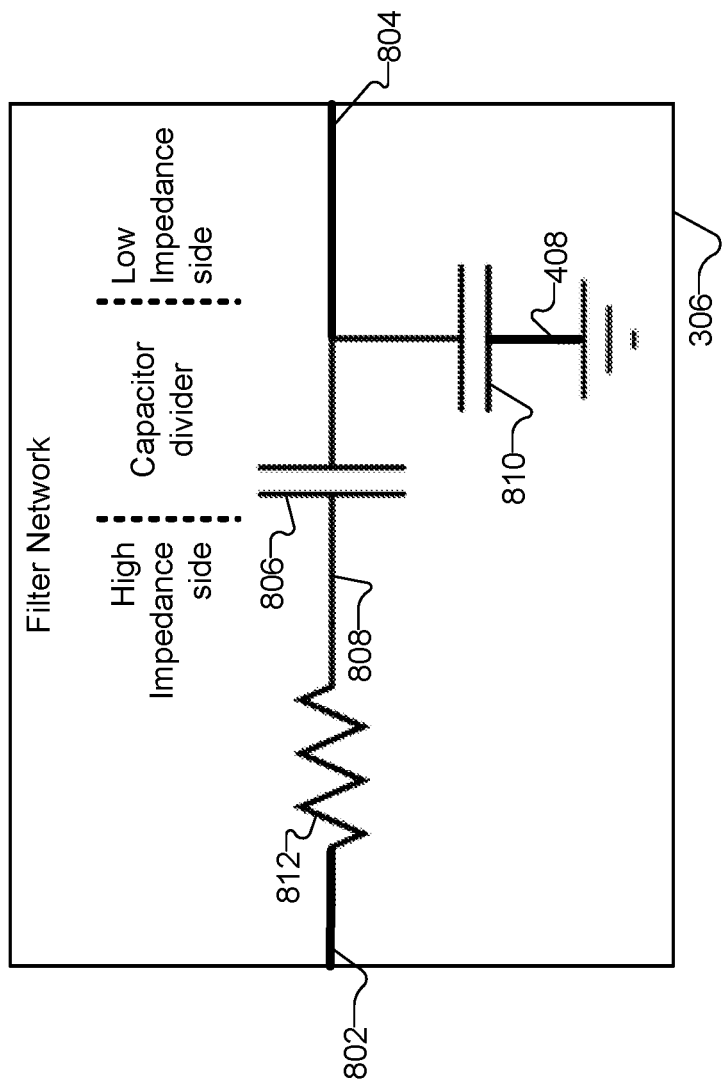

FIG. 8 illustrates another exemplary embodiment of filter network 306 used to process back telemetry signal 312 within cochlear implant 300. As shown, FIG. 8 includes similar components as FIG. 7, but the components of FIG. 8 are connected in a different configuration that may provide certain advantages described in more detail below. More specifically, like FIG. 7, FIG. 8 shows that filter network 306 may include an input node 802, an output node 804, and a plurality of impedance components including a capacitor 806, a capacitor 810, and a damping resistor 812. As described above with respect to capacitors 706 and 710 in FIG. 7, capacitors 806 and 810 may form a capacitor divider circuit configured to set a power level at which back telemetry signal 312 resonates to a predetermined target value that is lower than a natural power level that back telemetry signal 312 would have if filter network 306 included only capacitor 806 and not capacitor 810. As in FIG. 7, an inductive impedance divider circuit that includes inductors in place of capacitor 806 and capacitor 810 may be employed. For example, a capacitive impedance divider circuit (e.g., as shown in FIG. 8) may be used to set the power level to the predetermined target value in an embodiment where the back telemetry signal frequency is lesser than a forward telemetry signal frequency, while an inductive impedance divider circuit (not shown) may be used to set the power level to the predetermined target value in an embodiment where the forward telemetry signal frequency is lesser than the back telemetry signal frequency.

As further described above with respect to damping resistor 712 in FIG. 7, damping resistor 812 may set a quality factor of a resonator associated with filter network 306 to a predetermined target value that is lower than a natural quality factor that the resonator would have if the resonator included only capacitor 806 and an inductive component (e.g., inductor 510 of FIG. 5) and not damping resistor 812.

However, in contrast to FIG. 7, FIG. 8 illustrates that damping resistor 812 may be located on the high impedance side of the capacitor divider formed by capacitors 806 and 810 (e.g., at input node 802), rather than at a low impedance side of the capacitor divider (e.g., at output node 804) where capacitor 712 is located in FIG. 7. Accordingly, as shown in FIG. 8, filter network 306 may include damping resistor 812 connected between input node 802 and internal node 808, capacitor 806 connected between an internal node 808 and output node 804, and capacitor 810 connected between output node 804 and ground node 408.

There may be advantages to locating a damping resistor of a resonator either on the low impedance side of an impedance divider circuit (e.g., as illustrated by damping resistor 712 of FIG. 7) or on the high impedance side of the impedance divider circuit (e.g., as illustrated by damping resistor 812 of FIG. 8). For example, by locating the damping resistor on the low impedance side of the impedance divider circuit as shown in FIG. 7, the series resonator circuit may be relatively straightforward to analyze using basic circuit theory, facilitating component selection by a designer of the resonator by making it easy for the designer to determine a desired resistance value for the damping resistor to achieve a desired quality factor in the resonator and to determine desired capacitance values for the capacitors within the capacitor divider to achieve a desired power level. For example, in order to achieve a quality factor of approximately 5 to 7, the designer may determine using basic circuit theory that a value for damping resistor 712 should be a few ohms or a few tens of ohms (i.e., a particular value less than approximately 100 ohms).

Conversely, the analysis may be less straightforward for a damping resistor on the high impedance side of the capacitor divider circuit as shown in FIG. 8. In the circuit configuration of FIG. 8, damping resistor 812 may effectively convert capacitor 806 into a lossy capacitor with a reduced capacitance. As a result, more advanced circuit theory and/or other techniques may be employed to select component values for damping resistor 812 and capacitors 806 and 810 to achieve target values for important circuit parameters (e.g., quality factor, power level, etc.). For example, an approximation technique combined with a trial-and-error technique may be employed to determine component values for damping resistor 812 and capacitors 806 and 810. More specifically, approximate component values may be determined for each of damping resistor 812 and capacitors 806 and 810 using traditional circuit theory and then the component values may be iteratively modified to narrow in on the target values as actual results of the circuit parameters are simulated (e.g., using a circuit simulation tool) and/or measured (e.g., using actual components and measurement devices) in laboratory tests.

With component values selected to achieve predetermined target values of circuit parameters such as the quality factor and power level, the configuration of FIG. 8 may significantly facilitate the design of cochlear implant 300 by providing great flexibility in selecting and implementing components within cochlear implant 300. For example, because a desired quality factor (e.g., between approximately 5 and approximately 7) may be achieved with a resistance greater than a few tens of ohms (i.e., a particular value greater than approximately 100 ohms), more options for discrete resistors for implementing damping resistor 812 may be available as compared to discrete resistors for implementing damping resistor 712 of FIG. 7. In particular, manufacturers of discrete resistors may offer a greater selection of resistors with large resistance values in small packages (e.g., 0402 packages) desirable for cochlear implants. Similarly, the manufacturers may offer a greater selection of resistors with large resistances having tighter tolerances and/or less expensive prices. In some cases, more off-the-shelf resistors may be available with a resistance value suitably proximate to an exact desired value when the desired value is in the hundreds of ohms rather than in the single ohms or tens of ohms. Thus, flexibility in resistor selection may provide a significant cost savings since, in some cases, the alternative may be ordering resistors (e.g., custom-made resistors) with small resistance values and/or extra tight tolerances.

Large resistance values for damping resistor 812 may also be advantageous in that large resistances may be less susceptible to unavoidable and/or varying parasitic resistances that arise within various components of cochlear implant 300. For example, if parasitic resistances within cochlear implant 300 are determined to be between 0 and 10 ohms depending on unpredictable factors such as process variations in the manufacture of integrated circuit 302, the parasitic resistances may be difficult to account for with a damping resistor with a resistance in the range of 10 ohms, since the parasitic resistance may alter the total resistance by up to 100%. Conversely, if damping resistor 812 has a resistance of greater than 100 ohms, parasitic resistances of 0 to 10 ohms would alter the total resistance of damping resistor 812 by only up to 10%.

Moreover, locating damping resistor 812 at input node 802 of filter network 306 may provide significant flexibility in where and/or how damping resistor 812 may be implemented. For example, the resistance represented by damping resistor 812 in FIG. 8 may be implemented by one or more of a parasitic resistance of a driver component within driver 304 (e.g., driver components 410 and/or 412 of FIG. 4), an on-chip resistor within integrated circuit 302, a parasitic resistance associated with integrated circuit 302 or a trace leading out of integrated circuit 302, a discrete resistor external to integrated circuit 302, a parasitic resistance of a component within filter network 306 (e.g., capacitor 806), and any other source of parasitic or non-parasitic resistance within cochlear implant 300.

Figure 9:
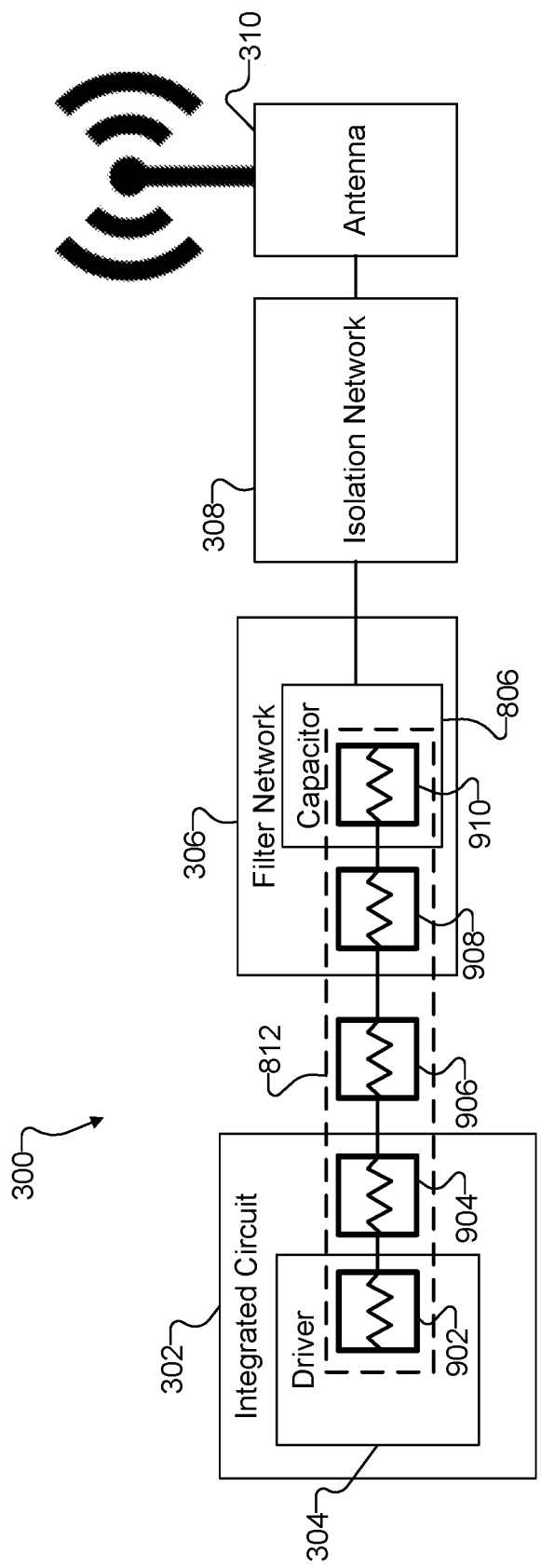
FIG. 9 illustrates various configurations of an exemplary damping resistor used in a resonator associated with an exemplary filter network within a cochlear implant according to principles described herein.

To illustrate, FIG. 9 illustrates various configurations of an exemplary damping resistor (e.g., damping resistor 812 of FIG. 8) used in a resonator associated with filter network 306 within cochlear implant 300. FIG. 9 illustrates the same block elements illustrated and described above in relation to FIG. 3, namely, integrated circuit 302 including driver 304, filter network 306, isolation network 308, and antenna 310. FIG. 9 also shows capacitor 806 within filter network 306. Capacitor 806 was illustrated and described above in relation to FIG. 8. Other details within each of the components of FIG. 3 that have been described above may be present in the components of FIG. 9 but are omitted for clarity.

As shown, FIG. 9 illustrates various locations within cochlear implant 300 at which resistance of damping resistor 812 (described above in relation to FIG. 8) may be located. Specifically, FIG. 9 shows several resistances (e.g., resistance 902, resistance 904, resistance 906, resistance 908, and resistance 910) that, together, may form damping resistor 812. While one or more parasitic or non-parasitic resistances could similarly combine to form damping resistor 712 (described above in relation to FIG. 7), it will be recognized that the unique placement of damping resistor 812 on the high impedance side of the capacitor divider in filter network 306 enables damping resistor 812 to be particularly flexible and configurable with resistances distributed across multiple components as shown in FIG. 9.

As illustrated by FIG. 9, damping resistor 812 may be distributed across resistances 902-910 in any way that suits a particular configuration. For example, as illustrated by resistances 902 and 904, a portion or the entirety of the resistance provided by damping resistor 812 may be implemented on integrated circuit 302.

For example, resistance 902 may represent a portion of the resistance provided by damping resistor 812 implemented on integrated circuit 302 that is generated by one or more components included within driver 304 (described above in reference to FIG. 4). Specifically, resistance 902 may represent parasitic resistances within driver components 410 and/or 412. Because parasitic resistance and corresponding inefficiency of driver components such as CMOS transistors may increase as the driver components decrease in size, a designer of driver 304 may normally be required to choose between designing driver 304 to be relatively small in size but relatively inefficient, and being relatively efficient but relatively large in size. In either case, the tradeoff between size and efficiency may be undesirable. However, when the parasitic resistance of the driver components is included within damping resistor 812 (e.g., as resistance 902), the designer may be able to avoid this undesirable tradeoff. Specifically, the driver components may be designed to be small with a relatively high parasitic resistance 902 because parasitic resistance 902 may contribute productively to damping the resonator associated with filter network 306 rather than merely adding wasteful inefficiency to driver 304.

As illustrated by resistance 904, at least some of the resistance of damping resistor 812 may be intentionally designed as an on-chip resistor within integrated circuit 302. For example, in certain embodiments, the entire resistance of damping resistor 812 may be implemented on integrated circuit 302 (e.g., using parasitic resistance 902 and/or on-chip resistance 904) such that filter network 306 does not include a discrete resistor. In this way, a designer of cochlear implant 300 may conserve space on the printed circuit board, which may be scarce, and/or may conserve other valuable resources. For example, eliminating a discrete resistor may help reduce manufacturing costs by eliminating a discrete component that would otherwise be maintained on a bill of material, purchased and stocked in inventory, and installed and tested during the manufacturing process of cochlear implant 300.

As illustrated by resistance 906, other parasitic resistances besides those in driver components 304 may also be included within damping resistor 812. For example, in some configurations, parasitic resistances may arise from component packaging of integrated circuit 302 (e.g., a resistance of a component lead), from a solder joint where integrated circuit 302 connects to a printed circuit board, from a trace within the printed circuit board connecting integrated circuit 302 with a discrete component within filter network 306 (e.g., a discrete resistor associated with damping resistor 812, a discrete capacitor associated with capacitor 806, etc.), or from any other component of cochlear implant 300 that carries current from driver 304 toward filter network 306. Any or all such parasitic resistances may be represented in FIG. 9 by resistance 906. By accounting for parasitic resistances encompassed in resistance 906, a designer may advantageously convert resistance 906 from a potentially deleterious parasitic resistance to a useful part of damping resistor 812 that may be productively used to facilitate setting a quality factor of a resonator associated with filter network 306 to a predetermined target value.

In other examples, some or a majority of the resistance provided by damping resistor 812 may be implemented by a discrete resistor external to integrated circuit 302. For example, as illustrated by resistance 908, filter network 306 may include a discrete resistor. The discrete resistor may be configured to provide all of a remainder of the desired resistance of damping resistor 812 that is not provided by parasitic resistances (e.g., resistances 902, 906, and 910). Alternatively, a discrete resistor associated with resistance 908 may be configured to account for parasitic resistances (e.g., resistances 902, 906, and 910) as well as an on-chip resistor associated with resistance 904. In certain examples, the discrete resistor external to integrated circuit 302 associated with resistance 908 may have a resistance greater than 100 ohms. As such, a variety of off-the-shelf discrete resistors may be available for a designer to select from such that the designer can find a discrete resistor with a resistance value closely approximating a desired resistance value as described above.

As illustrated by resistance 910, at least a portion of the resistance provided by damping resistor 812 may be implemented as a parasitic resistance of a discrete component of filter network 306 such as a discrete capacitor implementing capacitor 806. As described above with respect to parasitic resistances 902 and 906, a designer of cochlear implant 300 may account for parasitic resistance 910 to convert resistance 910 from a potentially deleterious parasitic resistance to a useful part of damping resistor 812 that may be productively used to facilitate setting the quality factor of the resonator associated with filter network 306.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
  a cochlear implant configured to be implanted within a patient and comprising:
    an integrated circuit configured to generate electrical stimulation for application to a cochlea of the patient, the integrated circuit including a driver coupled to a power supply node and to a ground node, the driver configured to generate at an output of the driver a back telemetry signal encoded with information to be transmitted over a wireless communication link to a sound processor located external to the patient; and a filter network comprising an input node serially coupled to the output of the driver, an output node, and a first plurality of impedance components including a damping resistor connected between the input node of the filter network and an internal node of the filter network, a first impedance component connected between the internal node of the filter network and the output node of the filter network, and a second impedance component connected between the output node of the filter network and the ground node.

2. The system of claim 1, wherein the filter network is associated with a series resonator having a quality factor set by the damping resistor to a predetermined target value, the target value lower than a natural quality factor of a series resonator associated with a filter network that includes the first capacitor and the second capacitor but lacks the damping resistor.

3. The system of claim 1, wherein the filter network is associated with an impedance divider circuit including the first capacitor and the second capacitor, the impedance divider circuit configured to set a power level at which the back telemetry signal resonates to a predetermined target value, the target value lower than a natural power level of a filter network that includes the first capacitor but lacks the second capacitor.

4. The system of claim 1, further comprising a lead coupled to the integrated circuit, the lead having a plurality of electrodes disposed thereon and configured to be implanted within the cochlea of the patient and to apply the electrical stimulation to the cochlea.

5. The system of claim 1, further comprising an antenna serially coupled to the output node of the filter network, the antenna facilitating telemetry over the wireless communication link between the cochlear implant and the sound processor by transmitting the back telemetry signal to the sound processor.

6. The system of claim 1, further comprising:

an isolation network serially coupled to the output node of the filter network, the isolation network including a second plurality of impedance components configured to isolate, from the filter network and the driver, a forward telemetry signal received by the cochlear implant from the sound processor; and an antenna serially coupled to an output node of the isolation network, the antenna facilitating telemetry over the wireless communication link between the cochlear implant and the sound processor by transmitting the back telemetry signal to the sound processor and receiving the forward telemetry signal from the sound processor.

7. The system of claim 6, wherein the second plurality of impedance components of the isolation network includes a third capacitor and an inductor, the third capacitor and the inductor connected in parallel between the output node of the filter network and an output node of the isolation network.

8. The system of claim 1, wherein the first impedance component and the second impedance component are capacitors.

9. The system of claim 1, wherein the first impedance component and the second impedance component are inductors.

10. The system of claim 1, wherein at least a portion of the resistance provided by the damping resistor is implemented on the integrated circuit.

11. The system of claim 10, wherein the damping resistor is implemented on the integrated circuit and does not include a discrete resistor.

12. The system of claim 10, wherein at least some of the portion of the resistance provided by the damping resistor implemented on the integrated circuit is generated by one or more components included within the driver.

13. The system of claim 10, wherein a majority of the resistance provided by the damping resistor is implemented by a discrete resistor external to the integrated circuit.

14. The system of claim 1, wherein at least a portion of the resistance provided by the damping resistor is implemented as a parasitic resistance of a discrete capacitor implementing the first capacitor.

15. A system comprising:

a cochlear implant configured to be implanted within a patient and comprising:

an integrated circuit configured to generate electrical stimulation for application to a cochlea of the patient, the integrated circuit including a driver coupled to a power supply node and to a ground node, the driver configured to generate at an output of the driver a back telemetry signal encoded with information to be transmitted over a wireless communication link to a sound processor located external to the patient; and a filter network comprising an input node serially coupled to the output of the driver, an output node, and a first plurality of impedance components including a first impedance component connected between the input node of the filter network and an internal node of the filter network, a second impedance component connected between the internal node of the filter network and the ground node, and a damping resistor connected between the internal node of the filter network and the output node of the filter network.

16. The system of claim 15, wherein the filter network is associated with a series resonator having a quality factor set by the damping resistor to a predetermined target value, the target value lower than a natural quality factor of a series resonator associated with a filter network that includes the first capacitor and the second capacitor but lacks the damping resistor.

17. The system of claim 15, wherein the filter network is associated with an impedance divider circuit including the first capacitor and the second capacitor, the impedance divider circuit configured to set a power level at which the back telemetry signal resonates to a predetermined target value, the target value lower than a natural power level of a filter network that includes the first capacitor but lacks the second capacitor.

18. A system comprising:

a microphone configured to detect audio signals presented to a patient;

a sound processor located external to the patient and configured to receive and process the audio signals detected by the microphone;

a cochlear implant configured to be implanted within the patient and to generate electrical stimulation as directed by the sound processor, the cochlear implant comprising:
an integrated circuit configured to generate electrical stimulation for application to a cochlea of the patient, the integrated circuit including a driver coupled to a power supply node and to a ground node, the driver configured to generate at an output of the driver a back telemetry signal encoded with information to be transmitted over a wireless communication link to the sound processor;
a filter network comprising an input node serially coupled to the output of the driver, an output node, and a first plurality of impedance components including
a damping resistor connected between the input node of the filter network and an internal node of the filter network,
a first capacitor connected between the internal node of the filter network and the output node of the filter network, and
a second capacitor connected between the output node of the filter network and the ground node;
an isolation network serially coupled to the output node of the filter network, the isolation network including a second plurality of impedance components configured to isolate, from the filter network and the driver, a forward telemetry signal received by the cochlear implant from the sound processor, the second plurality of impedance components of the isolation network including a third capacitor and an inductor, the third capacitor and the inductor connected in parallel between the output node of the filter network and an output node of the isolation network; and
an antenna serially coupled to the output node of the isolation network, the antenna facilitating telemetry over the wireless communication link between the cochlear implant and the sound processor by transmitting the back telemetry signal to the sound processor and receiving the forward telemetry signal from the sound processor; and
a lead coupled to the integrated circuit, the lead having a plurality of electrodes disposed thereon and configured to be implanted within the cochlea of the patient and to apply the electrical stimulation generated by the cochlear implant to one or more locations within the cochlea.

19. The system of claim 18, wherein the filter network is associated with a series resonator having a quality factor set by the damping resistor to a predetermined target value, the target value lower than a natural quality factor of a series resonator associated with a filter network that includes the first capacitor and the second capacitor but lacks the damping resistor.

20. The system of claim 18, wherein the filter network is associated with an impedance divider circuit including the first capacitor and the second capacitor, the impedance divider circuit configured to set a power level at which the back telemetry signal resonates to a predetermined target value, the target value lower than a natural power level of a filter network that includes the first capacitor but lacks the second capacitor.

\* \* \* \* \*